US006221670B1

(12) United States Patent
Cordell et al.

(10) Patent No.: US 6,221,670 B1
(45) Date of Patent: Apr. 24, 2001

(54) METHODS TO IDENTIFY β-AMYLOID REDUCING AGENTS

(75) Inventors: Barbara Cordell; Linda Slanec Higgins, both of Palo Alto, CA (US)

(73) Assignee: Scios Inc., Mountain View, CA (US)

( * ) Notice: Subject to any disclaimer, the term of this patent is extended or adjusted under 35 U.S.C. 154(b) by 0 days.

(21) Appl. No.: 08/821,876

(22) Filed: Mar. 21, 1997

(51) Int. Cl.$^7$ .......................... G01N 33/48; G01N 33/00
(52) U.S. Cl. .......................... 436/63; 435/7.1; 435/7.21; 435/7.9; 435/347; 435/373; 435/375; 800/3
(58) Field of Search .......................... 435/7.1, 7.9, 7.92, 435/325, 347, 373, 375, 378, 7.21; 436/503, 63; 424/9.2; 800/3

(56) References Cited

U.S. PATENT DOCUMENTS

| | | |
|---|---|---|
| 5,385,915 | 1/1995 | Buxbaum et al. . |
| 5,593,846 * | 1/1997 | Schenk et al. . |

OTHER PUBLICATIONS

Biological Abstracts, vol. 96, Philadelphia PA, Abs. No. 187108.
Chemical Abstracts, vol. 122, No. 9, Feb. 27, 1995, Columbus, OH, Abstract No. 102527.
Asami–Odaka et al., *Biochemistry* (1995), vol. 34, pp. 10272–10278.
Busciglio et al., *Proc. Natl. Acad. Sci. USA* (1993), vol. 90, pp. 2092–2096.
Chen et al., *Neuroscience Letter* (1991), vol. 125, pp. 223–251.
de Savage et al., *Science* (1989), vol. 245, pp. 651–653.
Diekman et al., *J. Neural Transm. Suppl.* (1994), vol. 44, pp. 61–71.
Esch et al., *Science* (1990), vol. 245, pp. 1122–1124.
Farber et al., *J. Neuroscience* (1995), vol. 15, pp. 7442–7451.
Gahwiler, *J. Neurosci. Meth.* (1981), vol. 4, pp. 329–342.
Gahwiler, *Neuroscience* (1984), vol. 11, pp. 751–760.
Gahwiler, *Trends Neuroscience* (1988), vol. 11, pp. 484–490.
Glenner and Wong, *Biochem. Biophys. Res. Commun.* (1984), vol. 120, pp. 885–890.
Goate et al., *Nature* (1991), vol. 353, pp. 844–846.
Haass et al., *Nature* (1992), vol. 359, pp. 322–325.
Higaki et al., *Neuron* (1995), vol. 14, pp. 651–659.
Higgins et al., *Ann. Neurol.* (1994), vol. 35, pp. 598–607.
Higgins et al., *Proc. Natl. Acad. Sci. USA* (1995), vol. 92, pp. 4402–4406.
Joachim et al., *Brain Res.* (1988), vol. 474, pp. 100–111.
Kang et al., *Nature* (1987), vol. 325, pp. 530–532.
Khachaturian, *Arch. Neurology* (1985), vol. 42, pp. 1097–1105.
Kitaguchi et al., *Nature* (1988), vol. 331, pp. 530–532.
London et al., *Proc. Natl. Acad. Sci. USA* (1996), vol. 93, pp. 4147–4153.

Maggio et al., *Proc. Natl. Acad. Sci. USA* (1992), vol. 89, pp. 5462–5466.
Masters et al., *Proc. Natl. Acad. Sci. USA* (1985), vol. 82, pp. 4245–4249.
Mattson et al., *Neuron* (1993), vol. 10, pp. 243–254.
Mori et al., *J. Biol. Chem.* (1992), vol. 267, pp. 17082–17086.
Mullan et al., *Nature Genet.* (1992), vol. 1, pp. 345–347.
Murrell et al., *Science* (1991), vol. 254, pp. 97–99.
Naidu et al., *J. Biol. Chem.* (1995), vol. 270, pp. 1369–1374.
Naslund et al., *Proc. Natl. Acad. Sci. USA* (1994), vol. 91, pp. 8378–8382.
Nitsch et al., *J. Neural Transm. Suppl.* (1994), vol. 44, pp. 21–27.
Ponte et al., *Nature* (1988), vol. 331, pp. 525–527.
Prelli et al., *J. Neurochem.* (1988), vol. 51, pp. 648–651.
Roher et al., *Proc. Natl. Acad. Sci. USA* (1993), vol. 90, pp. 10836–10840.
Saitoh t al., *Cell* (1989), vol. 58, pp. 615–622.
Schubert et al., *Neuron* (1989), vol. 3, pp. 689–694.
Seil, *Review in Neuroscience,* (1979), vol. 4, pp. 105–177.
Seubert et al., *Nature* (1992), vol. 359, pp. 325–327.
Shoji et al., *Science* (1992), vol. 258, pp. 126–129.
Sisodia et al., *Science* (1990), vol. 248, pp. 492–495.
Stoppini et al., *J. Neurosci. Methods* (1991), vol. 37, pp. 173–182.
Suzuki et al., *Science* (1994), vol. 264, pp. 1336–1340.
Tabaton et al., *Biochem. Biophys. Res. Commun.* (1994), vol. 200, pp. 1598–1603.
Tanzi et al., *Nature* (1988), vol. 331, pp. 528–530.
Teller et al., *Nature Med.* (1996), vol. 2, pp. 93–95.
Van Broeckhoven, *Eur. Neurology* (1995), vol. 35, pp. 8–19.
Vigo–Pelfrey et al., *J. Neurochem.* (1993), vol. 61, pp. 1965–1968.
Weidemann et al., *Cell* (1989), vol. 57, pp. 115–126.
Zhong et al., *J. Biol. Chem.* (1994), vol. 16, pp. 12179–12184.
Bruce et al *Proc. Natl. Acad. Sci*, 93: 2312–2316, Mar. 1996.*
Gähwiler et al. The World Congress pp109–115 "Organotypic Slice Cultures as In Vitro Model for Studying Long–Term Effects of Neurotoxic and Convulsant Substances in the Brain".*
Attenwill et al, Toxic, In Vitro, 7(5): 569–580, 1993.*
Boahr, B.A., Journal of Neuroscience Research, 42:294–305, 1995.*
Lannfelt et al, Behav. Brain Res, 57:207–213, 1993.*
Podlinsky et al, Neurobiology Aging 13, p. 562 col 3, paragraph 3.*
Relsenstein et al, Alzheimers and Parkinson's DiseaseI, Hanm, ed., Plenum Press, NY 1995 p. 406 col 1.*
Joachim et al , Alzheimer's Disease Assoc. Disorders, 6(1):7–34, 1992.*

* cited by examiner

*Primary Examiner*—Patricia A. Duffy
(74) *Attorney, Agent, or Firm*—Morrison & Foerster LLP

(57) ABSTRACT

The present invention provides methods that can be used to identify β-amyloid reducing compounds. The present invention is based on the use of organotypic brain slice culturing methods to simultaneously assess the toxicity and β-amyloid reducing activity of a test compound.

13 Claims, 4 Drawing Sheets

METHODS TO IDENTIFY β-AMYLOID REDUCING AGENTS

TECHNICAL FIELD

The present invention is in the field of assays used to identify agents for treating Alzheimer's disease. The present invention specifically provides methods for use in screening agents for use in reducing β-amyloid production/secretion/deposition, mainly in the treatment of Alzheimer's disease.

BACKGROUND ART

Alzheimer's disease (Alzheimer's) is a common age-related brain degenerative disease. The disease is characterized by progressive dementia together with the presence of characteristic neuropathological features. The formation of β-amyloid deposits or plaques is a hallmark and diagnostic feature of Alzheimerβs disease (Khachaturian (1985) *Arch Neurol* 42:1097–1105). A significant body of evidence suggests that the process of β-amyloid formation and deposition is directly linked to the development of this disease. For example, individuals with mutations in the gene encoding the β-amyloid precursor protein (β-APP) invariably develop Alzheimer's disease (Goate et al.(1991) *Nature* 353:844–846; Mullan et al. (1992) *Nature Genet* 1:345–347; Murrell *et al.* (1991) *Science* 254:97–99; Van Broeckhoven (1995) *Eur Neurol* 35:8–19). The β-amyloid peptide is a 39–43 amino acid protein (Glenner et al. (1984) *Biochem Biophys Res Commun* 120:885–890; Masters et al (1985) *Proc Natl Acad Sci USA* 82:4245–4249) which is capable of forming β-pleated sheet aggregates. These aggregating fibrils are subsequently deposited in the brain parenchyma or in the cerebrovasculature of the Alzheimer's disease victim.

The β-amyloid peptide is derived from a larger Type I membrane spanning protein, β-APP, which has several alternatively spliced transcripts (Kang et al. (1987) *Nature* 325:530–532; Ponte et al. (1988) *Nature* 331:525–527; Tanzi et al. (1988) *Nature* 331:528–530; Kitaguchi *el al.* (1988) *Nature* 331: 530–532; de Savage et al (1989) *Science* 245:651–653). The differentially spliced transcripts give rise to β-APP of 695, 714, 751, and 770 amino acids. The biological function of β-APP is not well understood although it appears to function in cell to cell contact, cell survival, and cell proliferation (Schubert *et al.* (1989) *Neuron* 3:689–694; Saitoh et al. (1989) *Cell* 58:615–622; Chen *et al.* (1991) *Neurosci Lett* 125:223–251; Mattson et al. (1993) *Neuron* 10:243–254).

A secreted form of β-APP is normally generated by proteolytic cleavage (Weidemann et al. (1989) *Cell* 57:115–126). This proteolytic cleavage occurs within the β-amyloid domain precluding β-amyloid formation (Esch et al. (1990) *Science* 248:1122–1124; Sisodia et al. (1990) *Science* 248:492–495). As a result of the cleavage, the bulk of β-APP is released from the cell and a carboxyl terminal fragment of ~8 kDa remains bound to the cell membrane. The enzyme(s) responsible for this non-amyloidogenic processing of β-APP is termed γ-secretase.

The formation of β-amyloid peptide is a normal physiological process. The peptide has been found to be naturally produced by cultured cells in vitro (Haass et al. (1992) *Nature* 359:322–325; Seubert et al (1992) *Nature* 359:325–327; Shoji et al. (1992) *Science* 258:126–129; and in vivo (Seubert *et al.* (1992) *Nature* 359:325–327; Vigo-Pelfrey et al. (1993) *J Neurochem* 61:1965–1968; Tabaton et al. (1994) *Biochem Biophys Res Commun* 200:1598–1603; Teller et al. (1996) *Nature Med* 2:93–95). The β-amyloid peptide appears to be a degradation by-product of intracellular catabolism of the non-secreted form of β-APP (Higaki et al. (1995) *Neuron* 14:651–659) and inhibiting its formation has no apparent deleterious consequences in vitro. There are two proteolytic processing steps required to produce the β-amyloid peptide: one produces the amino-terminus of the peptide mediated by an unidentified enzyme(s) referred to as β-secretase, the second forms the carboxyl-terminus of the peptide which is generated by an unidentified enyme(s) termed γ-secretase.

Attention in the Alzheimer's disease research community has been directed to inhibiting the processing of β-APP into β-amyloid peptide as an approach to novel therapeutic development for Alzheimer's disease. Neither the β- nor γ-secretase processing enzymes have been definitively identified or purified. No assay exists which contains pure β-APP and pure β-amyloid forming enzymes. Intact cultured cells provide a source of β-amyloid peptide. Screens for compounds which inhibit β-amyloid production have been developed based on measurement of β-amyloid production by cells in culture following application of a test compound. Toxicity of the compound is measured concomitantly. Test compounds which score as non-toxic inhibitors in such an assay are then tested for activity in animals. However, animal testing is laborious, expensive, and time consuming. In addition, many significant obstacles to obtaining inhibition of β-amyloid production in an animal exist which are absent in cell culture, including metabolism and clearance of the compound, limited access to the target organ (brain) imposed by the blood brain barrier, and selective cell toxicity. Thus, negative results in animal tests are difficult to interpret and are of limited use in informing structural design of other compounds. For these reasons it would be highly desirable to obtain a system for testing compounds for β-amyloid inhibiting activity and toxicity which resembled the complexity of the intact target organ, yet circumvented the technical difficulty of performing and interpreting whole animal testing experiments.

Organotypic slice culture methods have been developed for brain in which explants or sections of whole brain or, more commonly, a discrete anatomical brain structure such as hippocampus or cerebellum, are maintained in culture for extended periods of time (Seil (1979) *Review in Neuroscience* 4:105–177; Gahwiler (1981) *J. Neurosci Meth* 4:329–342; Gahwiler (1984) *Neuroscience* 11:751–760, Gahwiler (1988) *Trends Neurosci* 11:484–490). Recently significant improvements have been developed such that more reproducible results may be obtained through a simplified method (Stoppini et al., (1991) *J Neurosci Methods* 37:173–182). An essential feature of such cultures is the striking preservation of organotypic tissue architecture: cellular anatomy closely resembles that in the intact brain, to the extent that synaptic inputs and function mimic that of the normal situation, and development continues in neonatal brain slices. Typically, these preparations are used for electrophysiological studies investigating brain phenomena such as the biochemical basis of learning which require complex interactions of cells available only in the intact animal or organotypic slice cultures. Only two examples of use of organotypic brain slice cultures in Alzheimer's disease research are known in the art. London et al. ((1996) *Proc Natl Acad Sci* 93:4147–4153) looked at interactions of different brain cell types by applying monocytes pre-treated with synthetic amyloid to organotypic brain slice cultures, measuring cell survival. Nitsch, Wurtzman, and colleagues have examined the effects of neural stimulation by electrodes and neurotransmitters on brain circuitry (Diekman et al. (1994) *J Neural Transm Suppl* 44:61–71) and secretion of amyloid precursor protein (Nitsch et al (1994) *J Neural Transm Suppl* 44:21–27); Farber et al. (1995) *J Neurosci* 15:7442–7451).

The organotypic slice culture method has not been combined with assays for β-amyloid and cell viability to examine amyloid production and/or the effect of test compounds on its production. The present invention is based, in part, on combining organotypic slice culture methods with β-amyloid assays methods. The resulting methods of the present invention provides a rapid and efficient method for identifying compounds that can be used to treat Alzeimer's.

Prior art for testing compounds for inhibition of β-amyloid production relied on testing activity in whole animals, primary cells or cell lines in culture, broken cell or cell or tissue homogenates, or pure enzyme preparations. With the exception of the whole animal, none of these methods mimics the complexity of cell types and interactions found in the brain. Cellular interactions are known to affect β-amyloid precursor protein and β-amyloid production and secretion, and can be expected to affect availability, metabolism, and tolerance of compound in brain. Organotypic brain slice culture offers the full range of cell tppes present in brain with remarkably well preserved organization and cellular interactions. Thus, effects of test compounds on β-amyloid production and cellular viability and function are better predictors of in vivo effects than these measures taken on less complex single-cell systems. Candidate compounds may be eliminated prior to advancement to animal testing which have toxic effects or lack of efficacy that are evident in organotypic preparations, but which were not evident in cell culture systems.

Whole animal experiments are laborious, expensive, and time consuming to perform. In addition, relatively large amounts of test compound must be synthesized in order to dose animals. For example, under current animal testing protocols, a minimum of 7 animals/data point is generally required due to variation in animals and high sensitivity required of the assays. Each determination in organotypic culture requires a fraction of the number of animals as a similar determination in vivo: approximately 3 slices (20 are obtained/mouse or 30/rat) per data point, vs. 7 animals/data point, for a 70 fold reduction in the number of animals required. Dose response and time course studies performed in organotypic slice experiments facilitate better initial choices for in vivo dosing regimens, reducing the number of in vivo experiments with adjusted dosing regiments required.

Another major drawback of whole animal experiments in the number of variables which cannot be controlled and are difficult to assess. For example, if a compound is without effect, it may be due to rapid clearance from the blood, rapid metabolism, sequestration by a non-target tissue, or inability to penetrate the blood brain barrier. Dosing may be limited by toxicity to a sensitive non-target organ. Determining the contribution of these factors to a negative result is a major undertaking. Thus, negative results are not of use in generating structure-activity relationships to guide generation of improved compound structures. Organotypic slice culture eliminates or minimizes these variables since the blood brain barrier and other tissues are not present. Metabolism of compound is easily assessed by sampling media. Dose at the target organ is easily controlled.

DISCLOSURE OF THE INVENTION

The present invention provides methods that can be used to identify β-amyloid reducing compounds. The present invention is based on the use of organotypic brain slice culturing methods to simultaneously assess the toxicity and β-amyloid reducing activity of a test compound.

In general, β-amyloid reducing compounds can be identified by:
  preparing an oganotypic brain slice culture;
  assessing the viability of cells in said organotypic brain slice culture;
  applying a test compound to said organotypic brain slice culture;
  assessing the viability and β-amyloid production of (i) the treated organotypic brain slice culture and (ii) a non-treated organotypic brain slice culture; and
  identifying a compound that reduce β-amyloid production but does not decrease cell viability.

MODES OF CARRYING OUT THE INVENTION

General Description

Figure 1A:
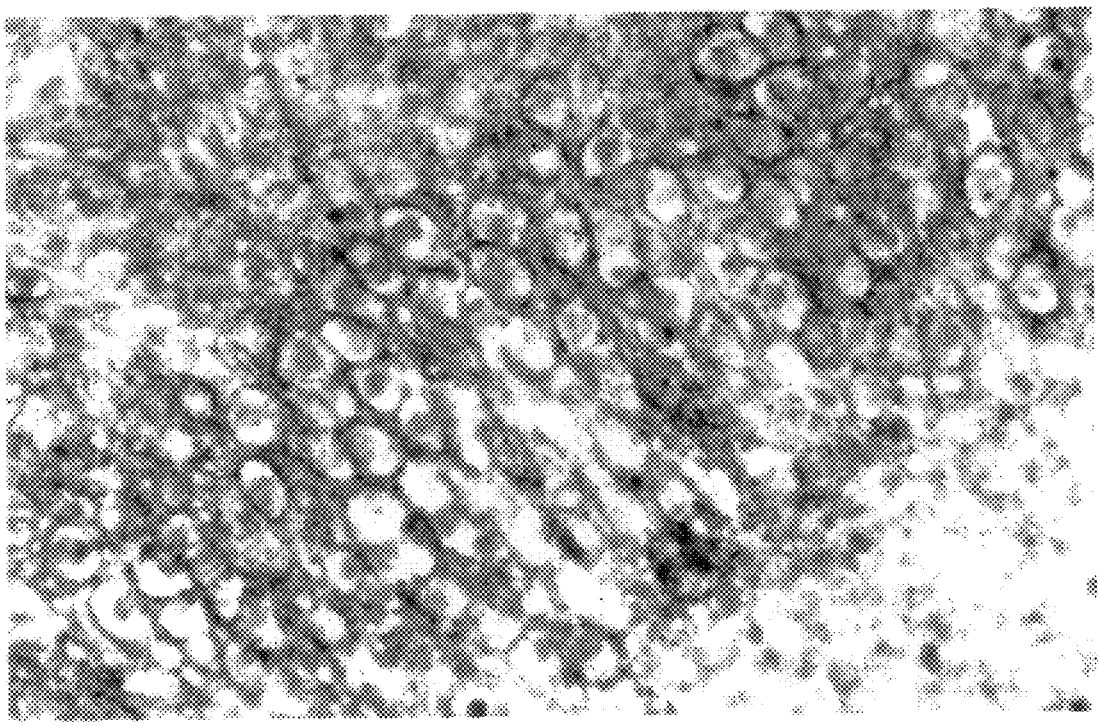
FIG. 1a shows a photomicrograph of a hippocampal organotypic slice prepared from rat, maintained in culture for 9 weeks, and stained using an antisynaptophysin monoclonal antibody.

The present invention provides methods that can be used to identify β-amyloid reducing compounds. The present invention is based on the use of organotypic brain slice culturing methods to simultaneously assess the toxicity and β-amyloid reducing activity of a test compound.

In general, β-amyloid reducing compounds can be identified by:
  preparing an oganotypic brain slice culture;
  assessing the viability of cells in said organotypic brain slice culture;
  applying a test compound to said organotypic brain slice culture;
  assessing the viability and β-amyloid production of (i) the treated organotypic brain slice culture and (ii) a non-treated organotypic brain slice culture; and
  identifying a compound that reduce β-amyloid production but does not decrease cell viability.

β-Amyloid and β-Amyloid Precursor Protein

As used herein, "β-amyloid peptide or protein" refers to any of the β-amyloid species of proteins. Such proteins are typically of ~4 kDa. Several different amino-termini and heterogeneous carboxyl-termini sequences have been observed based on characterization of the peptide β-amyloid protein from Alzheimer's disease tissue and from cultured cells (Glenner and Wong (1984) *Biochem Biophys Res Commun* 120:885–890; Joachim et al. (1988) *Brain Res* 474:100–111; Prelli et al. (1988) *J Neurochem* 51:648–651; Mori et al. (1992) *J Biol Chem* 267:17082–17806; Seubert et al. (1992) *Nature* 359:325–327; Naslund et al. (1994) *Proc Natl Acad Sci USA* 91:8378–8382; Roher et al. (1993) *Proc Natl Acad Sci USA* 90:10836–10840; Busciglio *et al.* (1993) *Proc Natl Acad Sci USA* 90:2092–2096; Haass et al. (1992) *Nature* 359:322–325). Specifically, with regard to the carboxyl-termini, the β-amyloid peptide has been shown to end at position 39, 40, 41, 42, 43, or 44 where position 1 is the aspartate of the β-amyloid sequence as defined by Glenner and Wong (1984) *Biochem Biophys Res Commun* 120:885–890.

The term "β-amyloid precursor protein" or "β-APP" refers to any of the differentially spliced isoforms of this protein including, but not limited to, the 695, 714, 751, and 770 amino acid isoforms (Kang et al (1987) *Nature* 325:530–532; Ponte et al. (1988) *Nature* 331:525–527; Tanzi et al. (1988) *Nature* 331:528–530; Kitaguchi et al (1988) *Nature* 331:530–532; de Savage et al. (1989) *Science* 245:651653). The term β-APP also includes naturally occurring human mutants of β-APP (Goate *et al.* (1991) *Nature* 353:844–846; Mullan et al. (1992) *Nature Genet* 1:345–347; Murrell et al. (1991) *Science* 254:97–99; Van Broeckhoven (1995) *Eur Neurol* 35:8–19); wild-type β-APP; mutant β-APP produced by cultured cells using recombinant DNA methodology; and to natural or artificial derivatives of β-APP which are capable of generating β-amyloid.

Organotypic Brain Slice Culture

As used herein, the term "organotypic brain slice culture" refers to sections or explants of brain tissue which are maintained in culture (Seil (1979) *Review in Neuroscience* 4:105–177; Gahwiler (1981) *J Neurosci Meth* 4:329–342; Gahwiler (1984) *Neuroscience* 11:751–760, Gahwiler (1988) *Trends Neurosci* 11:484–490; Stoppini et al. (1991) *J Neurosci Methods* 37:173–182). A skilled artisan can readily employ art known organotypic brain slice culture methods for use in the present invention.

Organotypic brain slice culture can employ sections of whole brain tissue or explants obtained from specific regions of the brain. Any region can be used to generate an organotypic brain slice culture. However, the preferred source of the organotypic brain slice culture is explants obtained from specific regions of the brain, preferably the hippocampus or cortex region.

Preparation of Organotypic Brain Slice Culture

Any mammal can be used as a tissue source for the explant that is used to generate the organotypic brain slice culture used in the present method so long as the animal can serve as a tissue source and the organotypic slice culture can be established and maintained for a period sufficient to conduct the present methods. Such mammals include, but are not limited to, rats, mice, guinea pigs, monkeys, rabbits and fetal humans.

The mammal used as a tissue source can be a wild-type mammal or can be a mammal that has been altered genetically to contain and express an introduced gene. Preferably, the animal will be a transgenic animal, such as a mice transgenic, that has been altered to express neural production of the β-amyloid precursor protein (Quon et al. (1991) *Nature* 35:598–607; Higgins et al. (1995) *Proc Natl Acad Sci USA* 92:4402–4406). Most preferably, the animal will be altered to express a β-amyloid precursor protein that is derived or based on human β-amyloid sequences.

The mammal used as a tissue source can be of any age. Preferably, the mammalian tissue source will be a neonatal mammal.

To obtain tissues for culturing from live animals, the animal is preferably quickly killed and decapitated, this generally being performed simultaneously. The brain is then rapidly removed to a dissection media buffered to physiological pH. An example of such a media is a minimal essential media (MEM) buffered with 10 mM Tris, pH 7.2, and supplemented with antibiotic.

The brain or desired brain region is then isolated under a dissecting microscope under aseptic conditions. Entire brain tissue can be used to establish an organotypic brain slice culture. Alternatively, a specific area or region of the brain can be used as an explant source. The preferred regions for the source of the organotypic brain slice culture for assessing β-amyloid production are the hippocampus and cortex.

Next small regions are separated from the tissue as slices or explants such that the surface to volume ratio allows exchange between the center of the tissue and the media. A variety of procedures can be employed to section or divide the brain tissues. For example, sectioning devices can be employed. The size/thickness of the tissue section will be based primarily on the tissue source and the method used for sectioning/division. For example, preferred segments are from about 400 to about 500 $\mu$m in diameter and are made using a tissue chopper, razor blade, or other appropriate sectioning/microtome blade.

After sectioning, sections are separated and damaged tissue removed. The sections of brain tissue are preferably manipulated in drops of dissecting media and placed on culture plate inserts in culture media. Excess media is drawn off, for example by using a tissue, and the culture is placed in an incubator.

The choice of culture media and culture conditions depends on the intended use, the source of tissue, and the length of time before the section is used in the present method. Examples of culture media include, but is not limited to 25% horse serum, 50% minimum essential media, 25% Hank's media, supplemented with antibiotic and L-glutamine. Examples of culture condition include, but are not limited to, 37° C., 5% $CO_2$.

Cultures can be maintained for as long as a few months, under the best of conditions. However, organotypic brain slice cultures are preferably used after they have stabilized following the trauma of transfer to culture, but before onset of decline. In general, it is preferable to use the slice cultures from about 1 week to about 4 weeks after they have been generated.

Assessment of Viability

After the organotypic brain slice culture is obtain, it is tested for viability prior to the application of a test compound. The viability/integrity of the organotypic slice culture is typically assessed at the initiation of each experiment in order to demonstrate the health of the preparation as well as to provide a measure of the amount of viable tissue present in the pretreated culture.

Any method known in the art for determining viability can be used. For example, such methods include, but are not limited to: visual inspection under a microscope; staining of sister cultures with vital dyes such as trypan blue; stains and immunohistochemical reagents specific for cell types or moieties present in normal and injured brain, such as silver stains, and antibodies to neurofilament, glial fibrillary acidic protein, S100, microtubule associated protein, normal or phosphorylated tau, and synaptic proteins; biochemical assessment of metabolic activity, such as with an MTT assay or of cellular leakiness, such as by a lactate dehydrogenase (LDH) assay; measurement of total or specific protein content; or assessment of cellular function, such as synaptic activity. Preferably, neural activity is apprised by measuring secretions such as soluble β-amyloid precursor protein secretion under basal conditions or neurotransmitter secretion upon stimulation. Stimulation can be accomplished by electrical stimulation, ionic depolarization (typically with high potassium), or application of neurotransmitter substance. Secreted substances typically measured are neurotransmitters present in the neurons such as acetylcholine, γ-amino butyric acid (GABA), glutamate, catecholamines, and neuropeptides. A skilled artisan can readily adapt any of the presently known viability test methods for use in the present invention.

Application of Test Substance

At the commencement of an experiment, an organotypic slice culture is typically transferred to a culture dish with media. The culture media can either have a test compound present prior to the introduction of the tissue section or a test compound can be added to the media after the tissue section has been place in the culture dish. In general, a test substance will be first dissolved in appropriate vehicle, such as, but not limited to, DMSO, water, physiological saline, or media, to make a stock solution and then diluted into the media. In general, a vehicle control test will be included when the present invention is used.

Preferably, a range of doses is tested. The range tested initially may be informed by prior knowledge of the effects of the substance or closely related substances on purified enzymes, β-amyloid production by cells in culture, or toxicity in other test systems. In the absence of such knowledge, the dose range is preferably from about 1 nM to about 100 $\mu$M. A skilled artisan can readily develop a testing range for any particular compound or series of compounds.

The compound is typically applied to the tissue section for about 4 hours to about 21 days, preferably from about 1 day to about 7 days. In the case of long term application, fresh media containing compound can be applied periodically; more frequently if rapid loss of compound due to chemical conversion or to metabolism is suspected.

Test Compound

Compounds that are assayed in the above method can be randomly selected or rationally selected or designed. As used herein, a compound is said to be randomly selected when the compound is chosen randomly without considering the structure of other identified active compounds. An example of randomly selected compounds is the use a chemical library, a peptide combinatorial library, a growth broth of an organism, or a plant extract.

As used herein, a compound is said to be rationally selected or designed when the compound is chosen on a nonrandom basis. Rational selection can be based on the target of action or the structure of previously identified active compounds. Specifically, compounds can be rationally selected or rationally designed by utilizing the structure of compounds that are presently being investigate for use in treating Alzheimer's disease.

The compounds of the present invention can be, as examples, peptides, small molecules, and vitamin derivatives, as well as carbohydrates. A skilled artisan can readily recognize that there is no limit as to the structural nature of the compounds of the present invention.

Assessment of Effects of Compound

At the conclusion of the test period, the period of time in which the test compound is contacted with the slice culture, the viability of cells in the slice culture and the level/degree of amyloid production by the treated and control cultures are assessed. A variety of art known methods can be employed to determine the amount of β-amyloid present. Such methods include, but are not limited to: determining the amount of β-amyloid secretion into the culture media using immunoprecipitation (Zhong et al (1994) *J Biol Chem* 16:1217912184; Higaki et al. (1995) *Neuron* 14:651–659); radioimmunoassay (Naidu et al. (1995) *J Biol Chem* 270:1369–1374); enzyme linked immunoassay (Vigo-Pelfrey et al. (1993) *J Neurochem* 61:1965–1968; Suzuki et al. (1994) *Science* 264:1336–1340; Asami-Odaka et al. (1995) *Biochemistry* 34:10272–10278) gel electrophoresis; and Western blotting techniques using concentrated or neat media conditioned by the treated and control organotypic brain slices. Soluble β-amyloid in the slice tissue can be measured by preparing a tissue homogenate and employing immunoprecipitation, radioimmunoassay, enzyme linked immunoassay, gel electrophoresis, or Western blotting techniques to detect amyloid. Deposited β-amyloid can be assessed biochemically or by counting amyloid deposits and plaques. Biochemically, insoluble material obtained from pellets of centrifugation of brain homogenates can be assessed as just described for brain homogenates. β-amyloid plaque and deposits can be visualized by standard histochemical stains such as silver, thioflavin S, and Congo red, by immunohistochemistry using anti-β-amyloid antibodies (Higgins et al. (1994) *Ann Neurol* 35:598–607; Higgins et al. (1995) *Proc Natl Acad Sci USA* 92:4402–4406), or by depositing [$^{125}$I-β-amyloid onto pre-existing deposits in the slice followed by autoradiography (Maggio et al. (1992) *Proc Natl Acad Sci USA* 89:54625466). It is well with the skill of the art to adapt β-amyloid detection methods for use in the present invention.

In practicing the present invention, β-amyloid secretion from brain tissue, β-amyloid deposition in brain tissue, and β-amyloid present in brain tissue can be determined independently in separate experiment/treatments, or alternatively, two or more of the β-amyloid classes can be determined from a single test sample. In general, it is preferable to detect β-amyloid secretion from brain tissue, β-amyloid deposition in brain tissue and β-amyloid present in brain tissue for each test compound.

In addition to measuring β-amyloid production, it is preferred that a measurement is made of the amount of viable tissue in the slices producing the amyloid. This measurement is used to normalize the values for β-amyloid in the media and as a means for determining the toxicity of a test agent. In general, the viability assay is the one employed at the initiation of the experiment. Preferably, an assay that does not damage the slice is used both at the initiation and conclusion of the test period. Such a use provides the highest accuracy and allows efficient assessment of toxicity of the compound. If this is not possible, either a survival assay is used at the initiation of the experiment or an assay that destroys the slices is performed on sister a culture.

Identification of β-Amyloid Reducing Compounds

The agents used in the present method will be classified by the degree they reduce β-amyloid production and the degree of toxicity displayed. The most preferred compounds identified using the present method with be non-toxic, showing no reduction in viability between treated and non-treated cultures. However, low toxicity levels may be tolerable for certain uses (e.g., in initial compound testing and design). The preferred compounds will reduce β-amyloid secretion/deposition/production by more than 50%. More preferably, β-amyloid secretion/deposition/production will be reduced by more than 90%, most preferably eliminating all β-amyloid secretion/deposition/production.

These examples are intended to illustrate but not to limit the invention.

EXAMPLE 1

Compound Testing with Rat Organotypic Brain Slice Cultures

Preparation of Cultures

Eight day old neonatal rat pups were quickly decapitated with scissors, serrated on one edge, in an aseptic fume hood. The brain was rapidly removed to buffered dissection media containing 100 ml MEM, 1 ml penicillin/streptomycin, 1 ml Tris 100×stock (10 mM final, pH 7.2), sterile filtered and chilled. The hippocampi were isolated under a dissecting microscope and transported in dissection media to a sterile fume hood. Tissue was positioned on the stage of a MacIllwain tissue chopper with a sterile paint brush, and 400 μm sections were made. Approximately 30 sections per animal were be obtained. Sections were separated by vigorously swirling the petri dish containing the sections in culture media, containing 25% horse serum, 25% Hank's media, 50% minimal essential media, 1 ml penicillin/streptomycin, 0.5 ml L-glutaine. Sections were inspected with a dissecting microscope and damaged tissue removed. The selected sections were manipulated in drops of dissecting media with Pasteur pipettes which had been scored and broken, then fire polished, to produce appropriate diameter bores, and placed on millipore culture plate inserts set into 35 mm plate containing 1 ml culture media or 6 well plates containing 1.2 ml culture media. Plates containing inserts and media had been pre-equilibrated to 37° C. and 5% $CO_2$. Three to six slices were positioned on each insert. Excess media was drawn off the slice, and the culture placed in a 37°, 5% $CO_2$ incubator. Cultures were maintained for up to 3 months. Media was changed at 24 hours, and at 3–4 day intervals following. Media conditioned by the hippocampal organotypic slice culture was saved for assay.

Characterization of Cultures

Organotypic brain slice cultures were inspected daily for the first week in culture and every few days thereafter. During the first week, organotypic brain slice cultures flatten and spread, although tissue architecture is retained. Growth cones were observed emerging from the edge of the slices, and glial cells appeared at the edge of the slice during the first week. Growth cones were subsequently retracted. Glial cells remained at the edge of slices but did not grow over the body of the slice. Cellular organization and composition were assessed in slices which had been maintained in culture for one week intervals from 1 to 8 weeks to confirm that cellular morphology, composition, and organization resembled that of the intact hippocampus.

Immunohistochemistry was performed using synaptophysin, growth associated protein 43 (GAP-43), microtubule associated protein 2 (MAP-2), and neurofilament 200 antibodies to visualize neurons and S-100 and glial acidic fibrillary protein (GFAP) antibodies to visualize glial cells, according to the following protocol:

Organotypic slice cultures were manipulated on the culture insert. The insert was moved using tweezers between culture plates containing the appropriate treatment. First, media was washed from the culture with several rinses of phosphate buffered saline PBS: (100 mM NaCl, 10 mM $NaPO_4$, pH 7.4). Tissue was fixed by incubation for 2 hours at room temperature with freshly prepared 4% paraformaldehyde in PBS. Fix was removed with 2×2 minute rinses in PBS. Endogenous peroxidase activity was quenched by 30 minute room temperature incubation with 0.3% hydrogen peroxide, rinsed 10 minutes in PBS and 10 minutes in PBS with 0.2% gelatin. Next they were blocked in PBS/10% goat serum/0.1% Nonident P-40 for one hour and rinsed 2×10 min in PBS. Primary antibody was applied at the indicated dilution made in PBS containing 0.2% gelatin and incubated overnight in a humidified chamber. After 3×3 minute rinses in PBS/gelatin, cultures were incubated with a 2° antibody, (either anti-mouse or anti-rabbit as appropriate, provided with Vectastain Elite immunohistochemistry kit) in PBS/gelatin at 37° for 30 minutes. Vectastain Elite ABC reagent was prepared according to manufacturer's instructions. Following 3×3 minute rinses with PBS/0.2% gelatin, cultures were incubated at 37° for 30 minutes with the ABC reagent. Immunoreactivity was visualized by development with a 3,3'-diaminobenzidine (DAB) kit from Vector labs and prepared according to directions and rinsed with water. Dehydration was accomplished by 2 minute incubations in 35%, 50%, 70%, 90%, and 2×100% ethanol. Cultures were counterstained for 2–4 minutes with hematoxylin, and rinsed with water until clear. Destaining of insert itself with 0.5% hydrochloric acid in 70% ethanol for 30 sec and tap water rinses followed. After air drying, individual slices were cut out of the insert and mounted on microscope slides using gel mount, covered with cover slips and sealed with nail polish. Representative photomicrographs are provided in FIG. 1.

Figure 2:
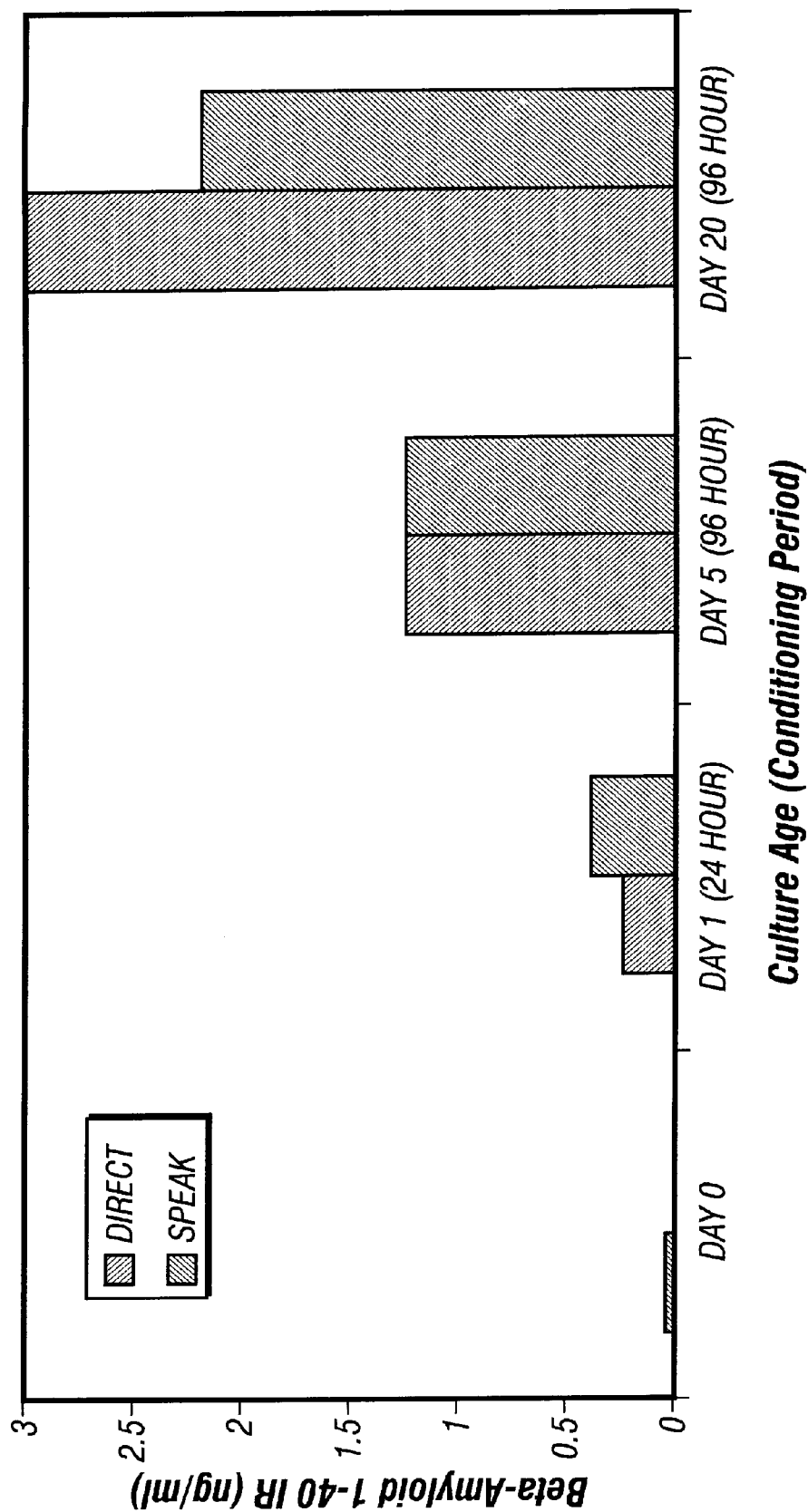
FIG. 2. β-amyloid 1–40 secretion from hippocampal organotypic slice cultures.

Cresyl violet, hematoxylin, and toluidine blue staining were performed by fixing cultures in paraformaldehyde as described above. Hematoxylin (Sigma) was applied for 2–4 minutes, after which cultures were rinsed with water and cleared in ethanol as described above. Cresyl violet and toluidine blue were made as stock dye solution of 0.1% in distilled water. Staining solution was made as 20% in 0.2 M acetate buffer, pH 4.45:3 parts 0.2 M acetic acid, 2 parts 0.2 M sodium acetate, 5 part water. Staining time was 20 minutes for both dyes. Cultures were rinsed with water, dehydrated in ethanol, dried, and mounted as described above.

β-amyloid 1-40 secretion into media was examined by collecting media conditioned during the initial 24 hours in culture, during day 1 through 4 in culture, and during day 16 through 20 in culture. Aliquots of the conditioned media were assayed using a sandwich ELISA to measure β-amyloid 1-40 in one of two ways. First, duplicate 100 μl aliquots were assayed directly in the ELISA. Second, 3 ml pools of media from 3 separate culture wells were concentrated and simultaneously separated from some other components by application to Sep-Pak C18 columns and elution in acetonitrile. The 50% elution fraction, previously shown to contain amyloid, was collected, dried, resuspended in a small volume of buffer, and assayed in the ELISA. Results of the two assays agreed closely and demonstrate easily measurable levels of β-amyloid 1-40 in conditioned media, even in the absence of a concentration step (see FIG. 2).

Application of Compound

Two test compounds were selected which had scored positive for β-amyloid lowering activity in cell culture assays and had scored as non toxic on the same cells. These compounds had been tested in guinea pigs, and were found to be highly toxic to brain tissue. The present example was used to show that a slice assay is a better predictor of in vivo activity than the cell culture assay.

Test compounds were dissolved in DMSO to produce 100×stock solutions. Stocks were further diluted in culture media to give final concentrations of 0, 1 $\mu$M, and 100 $\mu$M compound. Media was pre-equilibrated in plates at 37°, 5% $CO_2$. Culture inserts holding 3 rat organotypic brain slices obtained from 8 day old rats and maintained in culture for 2 weeks were transferred to the media containing test solution. Media was collected and fresh media containing test solution provided at 24 hour intervals for 10 days. Organotypic brain slice cultures were observed daily. Visual inspection revealed a loss of tissue integrity revealed by darkened patches in the center of the slice, loss of cellular layer organization, and ultimately by loss of tissue at the edge of the slice.

Assessment of Toxicity

Toxicity was assessed visually under dissecting and inverted light microscopes. At the conclusion of the experiment, cultures were processed for anti-synaptophysin antibody immunoreactivity. Both test compounds had scored as non-toxic over the concentration range tested in this experiment in a cell based assay using an assay of mitochondrial function (MTT assay) to measure viability. In vivo testing of the first compound showed significant toxicity as scored by histochemistry of brain sections from treated guinea pigs. Visual inspection of treated organotypic slice cultures revealed overt toxicity by 5–6 days of treatment and a severely necrotic appearance at the conclusion of the 10 day experiment. Immunohistochemistry confirmed this assessment. Thus, the organotypic slice assay was a better predictor of in vivo results than the cell based assay. The second compound also scored as non-toxic in the cell based assay, and had a slightly less severe but still marked toxic effect on the organotypic slice cultures. As predicted by organotypic slice culture assay results, this compound was less toxic than the first although clear toxicity was observed.

Figure 1B:
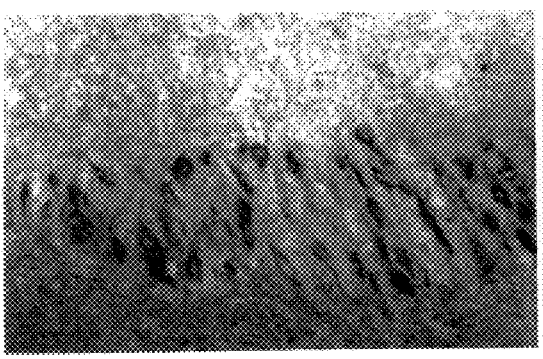
FIG. 1b is a photomicrograph of a hippocampal organotypic slice prepared from rat maintained in culture for 4.5 weeks, and stained using an antineurofilament 200 monoclonal antibody.
Figure 1C:
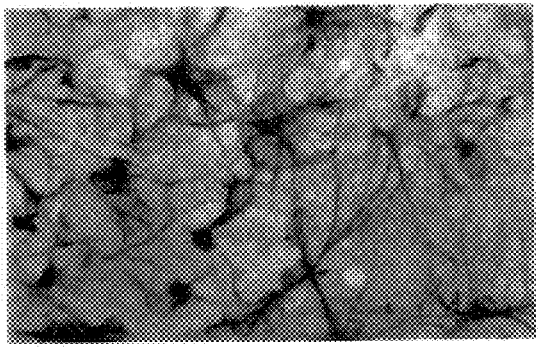
FIG. 1c is a photomicrograph of a hippocampal organotypic slice prepared from rat maintained in culture for 10 weeks, and stained using an antiglial fibrullary acidic protein (GFAP) monoclonal antibody.

Detailed Description of FIG. 1

Organotypic slice cultures were manipulated on the culture insert during staining procedures using tweezers to move the insert between culture plates containing the appropriate treatment. First, media was washed from the culture with several rinse of phosphate buffered saline PBS: (100 mM NaCl, 10 mM $NaPO_4$, pH 7.4). Tissue was fixed by incubation for 2 hours at room temperature with freshly prepared 4% paraformaldehyde in PBS. Fix was removed with 2×2 minute rinses in PBS. Endogenous peroxidase activity was quenched by 30 minute room temperature incubation with 0.3% hydrogen peroxide, rinsed 10 minutes in PBS and 10 minutes in PBS with 0.2% gelatin. Next they were blocked in PBS/10% goat serum/0.1% Nonident P-40 for one hour and rinsed 2×10 min. in PBS. Primary antibody was applied at the indicated dilution made in PBS containing 0.2% gelatin and incubated overnight in a humidified chamber. After 3×3 minute rinses in PBS/gelatin, cultures were incubated with a 2° antibody (either antimouse or antirabbit as appropriate, provided with Vectastain Elite immunohistochemistry kit) in PBS/gelatin at 37° for 30 minutes. Vectastain Elite ABC reagent was prepared according to manufacturer's instructions. Following 3×3 minute rinses with PBS/0.2% gelatin, cultures were incubated at 37° for 30 minutes with the ABC reagent. Immunoreactivity was visualized by development with a 3,3'-diaminobenzidine (DAB) kit from Vector labs and prepared according to directions and rinsed with water. Dehydration was accomplished by 2 minute incubations in 35%, 50%, 70%, 90%, and 2×100% ethanol. Cultures were counterstained for 2–4 minutes with hematoxylin, and rinsed with water until clear. Destaining of insert itself with 0.5% hydrochloric acid in 70% ethanol for 30 sec and tap water rinses followed. After air drying, individual slices were cut out of the insert and mounted on microscope slides using gel mount, covered with cover slips and sealed with nail polish. The top panel shows a representative photomicrograph of a hippocampal organotypic slice prepared from rat, maintained in culture for 9 weeks, and stained using an antisynaptophysin monoclonal antibody. A CA-1 field is shown at 20×. The lower left panel is a representative photomicrograph of a hippocampal organotypic slide prepared from rat, maintained in culture for 4.5 weeks, and stained using an antineurofilament 200 monoclonal antibody, and photographed at 20×. The lower right panel is a representative photomicrograph of a hippocampal organotypic slice prepared from rat, maintained in culture for 10 weeks, and stained using an antiglial fibrillary acidic protein (GFAP) monoclonal antibody, and photographed at 40×. The immunoreactivity shown are standard markers for synapses, neuronal soma, and astrocytes, respectively. Normal cell and tissue morphology are demonstrated.

EXAMPLE 2

Assessment of Transgenic Mouse Organotypic Slice Cultures

Preparation of cultures. Ten day old mouse pups transgenic for the 751 amino acid isoform of human $\beta$-amyloid precursor protein ($\beta$-APP), programmed for neural expression by the neuron specific enolase promoter were used as tissue source for hippocampal organotypic slice cultures. Cultures were prepared as for rat brain slice organotypic cultures described in Example 1.

Assessment of viability. Transgenic mouse brain slice cultures were observed visually with a dissecting and an inverted light microscope every other day. At various times, slices were taken for histochemistry using cresyl violet and hematoxylin to discriminate cell morphology and organotypic anatomy, and synaptophysin and GFAP immunohistochemistry to assess the morphology of neurons and glia, respectively.

Figure 3:
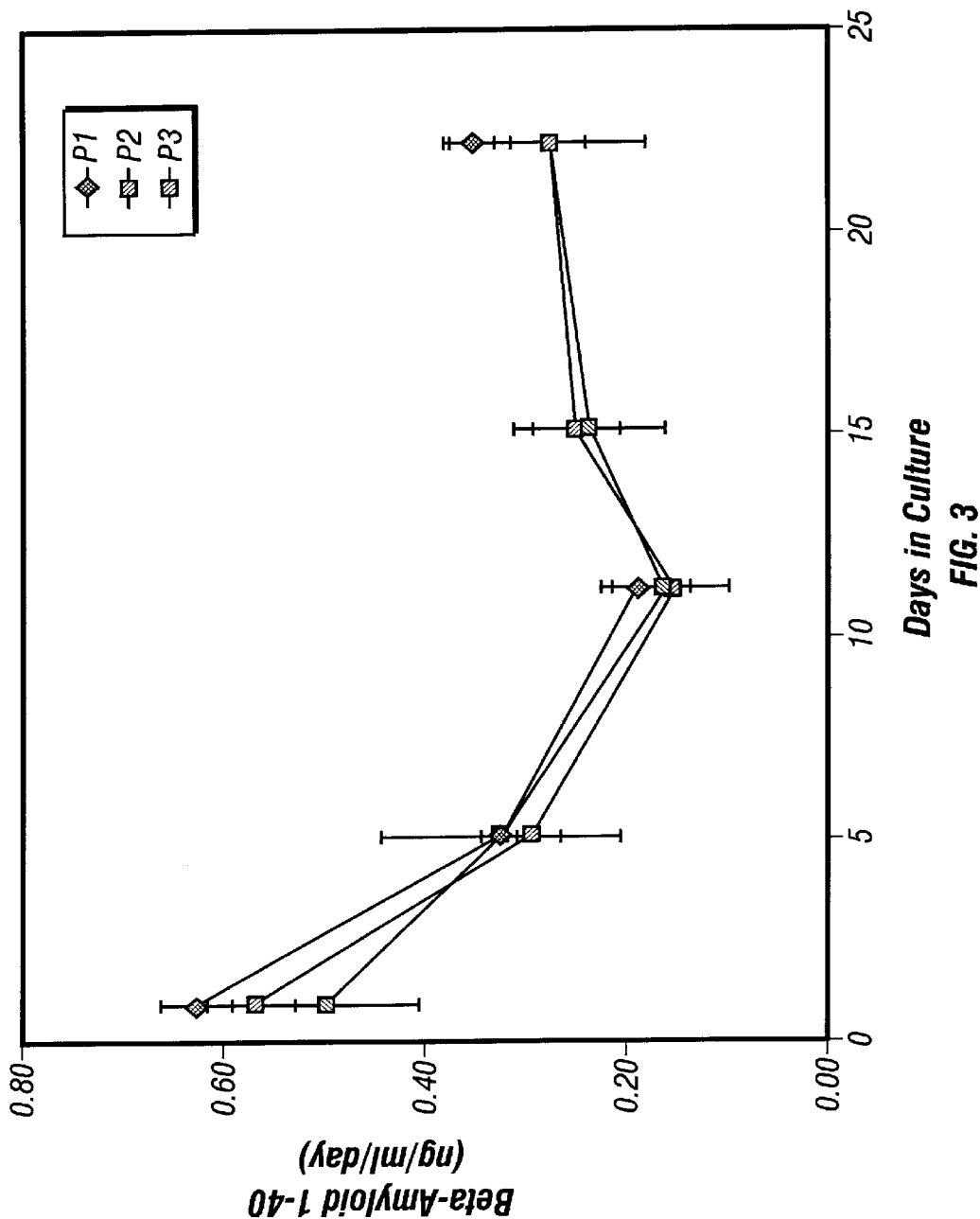
FIG. 3. β-amyloid 1–40 secretion from hippocampal organotypic slice cultures prepared from mice transgenic for β-APP751.

Assessment of $\beta$-amyloid secretion. Conditioned media was collected from individual culture wells containing 3 organotypic hippocampal slices during the first 24 hour period in vitro, and subsequently during 3–4 day intervals. Duplicate 100 $\mu$l samples of these conditioned media samples were assayed for 3 culture wells each for hippocampal slice cultures derived from 3 donor animals directly in sandwich ELISAs which detect $\beta$-amyloid 1-40 or $\beta$-amyloid 1-42. Results of this experiment demonstrate that amyloid secretion from transgenic mouse organotypic hippocampal cultures [1] is easily detectable at a level that allows measurement of inhibitory activity [2] is stable from 5–20 days [3] is produced at a level independent of the individual donor animal and [4] shows acceptably low variability between culture wells. Results from the $\beta$-amyloid 1-40 ELISA assay are shown in FIG. 3.

EXAMPLE 3

Compound Testing with Transgenic Mouse Organotypic Slice Cultures

Preperation of cultures. Hippocampal organotypic slice cultures were prepared as described in example 2, from 10 day old mice transgenic for the 751 amino acid isoform of human β-amyloid precursor protein (β-APP), programmed for neural expression by the neuron specific enolase promoter and maintained in culture for 10 days.

Assessment of viability. Cultures were observed visually approximately every other day. At the commencement of compound testing, on day 10 in culture, a quantitative assessment of viability was made. Brain slices were depolarized by application of high potassium (54 mM) media for 5 minutes. Inserts were passed through 2×2 min washes in media pre-equilibrated at 37°, 5% $CO_2$, and returned to the incubator. High potassium media conditioned by the slices during the depolarization period contains moieties released by synaptic vesicles. This media was divided into two aliquots and assay for γ-amino butyric acid (GABA) and glutamate, two peptide neurotransmitters present in the hippocampus. Media was conveniently assayed using ELISAs developed with commercially available antibodies specific for GABA and glutamate. The third aliquot was used to assay for acetylcholine (ACh), a neurotransmitter affected early in AD hippocampus, using a radiolabeled cholinergic antagonist displacement assay employing ACh-receptor bearing membranes. These assays provide a quantitative measure of the amount of viable tissue present on each insert, demonstrates intact synaptic activity, and does not harm the cultures.

Application of test compound. Test compound was dissolved in DMSO to produce a 100×stock solution, and further diluted in culture media to appropriate final concentrations. These were usually 100 nM to 100 μM compound, unless previous information about the activity or toxicity of the compound dictates otherwise. A 1% DMSO control for the final concentration of vehicle was included. Media was pre-equilibrated at 37°, 5% $CO_2$, before the culture insert was transferred to the new plate, and media was changed every 48 hours to provide fresh compound. Conditioned media was saved for assessment. Cultures were observed visually daily. The application of test compound continued for 10 days.

Assessment of viability. At the conclusion of the test period, conditioned media from the final test interval was collected and synaptic activity was assessed by depolarization in high potassium medium followed by measurement of GABA and glutamate released, as described above.

Assessment of β-amyloid lowering activity. Conditioned media from each test period interval was assayed for β-amyloid level using an ELISA assay. Data generated by this method provides a dose response relationship as well as a time course for each dose tested. Since differing amounts of viable tissue can be present on each culture insert to serve as source of amyloid, the values for β-amyloid in the conditioned media were normalized using the values for transmitter released at the initiation of the experiment. Toxicity was evaluated by comparing transmitter release values at the initiation and at the conclusion of the experiment. Compounds causing a decrement in transmitter release values at the conclusion of the experiment relative to the beginning were considered to have a toxic effect. In this case, decrement in β-amyloid levels can be attributed to toxicity rather than specific effects on β-amyloid production. Deposited β-amyloid was scored by immunohistochemistry using anti-β-amyloid antibody mAb 4.1 to score the number of amyloid deposits and plaques per area in treated vs. control slices.

EXAMPLE 4

Compound Testing with Transgenic Mouse Organotypic Slice Cultures

Preparation of cultures. Hippocampal organotypic slice cultures are prepared from 10 day old mice transgenic for the 751 amino acid isoform of human β-amyloid precursor protein (β-APP), programmed for neural expression by the neuron specific enolase promoter as described in Example 2, and maintained in culture for 6 weeks.

Figure 4:
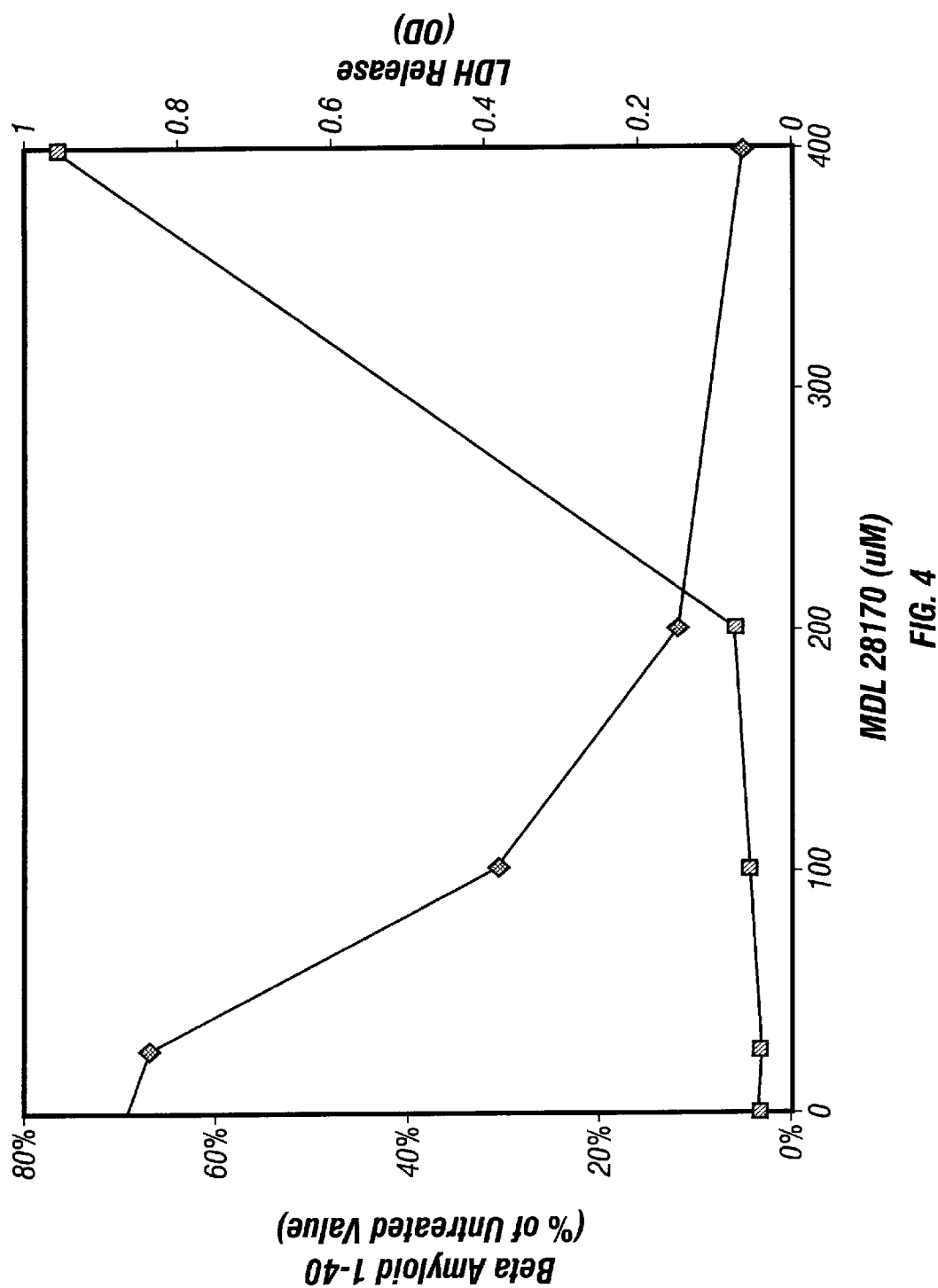
FIG. 4. Assessment of test compound MDL 28170 on the viability and β-amyloid secretion of organotypic slice cultures.

Detailed description of FIG. 4. Hippocampal organotypic slice cultures were prepared from mice transgenic for β-APP751. On day 21 in vitro, organotypic cultures were washed with media twice, and duplicate wells were incubated for a 3-day conditioning period in media supplemented with 25 μM to 400 μM MDL 28170, a protease inhibitor shown to inhibit total β-amyloid production in cell culture with an $IC_{50}$ of 100 μM. MDL 28170 was applied from 100×stock solutions prepared in DMSO. Control culture received only DMSO. Conditioned media was collected at day 24 and assayed in duplicate for β-amyloid 1-40 using a sandwich ELISA. Organotypic cultures were washed with serum free media twice and incubated for an additional 24 hours in serum free media in the continued presence of MDL 28170. This conditioned media was assayed for lactate dehydrogenase (LDH) activity. LDH is a ubiquitous cytosolic enzyme released into conditioned media only by unhealthy cells and is an index of viability and toxicity. High levels of LDH activity in serum require measurements to be made in serum free conditioned media. Data points shown were calculated by first taking the mean of duplicate ELISA values for each well, and then calculating the mean of the values for the duplicate treatment wells.

Assessment of β-amyloid inhibitor activity and toxicity. Cultures are observed visually approximately every other day. Prior to the commencement of compound testing, on day 18 in culture, a three day test period was initiated in which media was conditioned by the untreated cultures. This media was collected and assayed for β-amyloid 1-40 and 1-42 levels using sensitive ELISAs. Organotypic cultures were then washed with media twice, and incubated for a further 3 day conditioning period in media supplemented with 25 μM to 400 μM MDL 28170, a protease inhibitor shown to inhibit total β-amyloid production in cell culture with an $IC_{50}$ of 100 μM. MDL 28170 was applied from 100×stock solutions prepared in DMSO. Control culture received only DMSO. After conditioned media was collected at day 21, organotypic cultures were washed with serum free media twice and incubated for an additional 24 hours in serum free media in the continued presence of MDL 28170. This conditioned media was assayed for lactate dehydrogenase (LDH) activity. LDH is a ubiquitous cytosolic enzyme released into conditioned media only by unhealthy cells and is an index of viability and toxicity. High levels of LDH activity in serum require measurements to be made in serum free conditioned media. Next, organotypic hippocampal slice cultures were rinsed in media containing serum but no drug, and allowed to condition fresh media for 3 days. This media was assayed for β-amyloid 1-40 and 1-42 with the same ELISAs to determine whether MDL activity is reversible in the organotypic brain slice system, as it is on cultured monotypic cells. This assay was followed by a 24 hour conditioning period with serum free media to determine whether toxic effects of MDL 28170 were also reversible. FIG. 4 illustrates that the $IC_{50}$ of MDL 28170 is 100 μM for β-amyloid production by transgenic mouse hippocampal organotypic slice culture, as it is for a variety of monotypic cell cultures. In addition, inhibition was demonstrated in the absence of toxicity, which was not apparent by visual inspection or by LDH assay until the concentration of the test compound reached 400 μM.

What is claimed is:

1. A method for identifying a beta amyloid reducing agent which method comprises
   (a) contacting a test compound with a test organotypic brain slice culture and measuring (1) the viability and (2) the amount of beta amyloid production of said test organotypic brain slice culture; and,
   (b) measuring (1) the viability and (2) the amount of beta amyloid production of a control organotypic brain slice culture; and
   (c) identifying as a beta amyloid reducing agent a test compound which reduces the amount of beta amyloid production in said test culture as compared to said control culture, but does not reduce viability of said test culture in comparison with said control culture;
   wherein said test organotypic brain slice culture and control brain slice culture contain viable cells and are derived from a mammal.

2. The method of claim 1, wherein said mammal is selected from the group consisting of rats, rabbits, guinea pigs and mice.

3. The method of claim 2 wherein said mammal is a trangenic mouse.

4. The method of claim 3 wherein said mouse neurally expresses beta amyloid protein from said transgene.

5. The method of claim 4 wherein said beta amyloid protein is human.

6. The method of claim 1, wherein said organotypic brain slice culture is an explant obtained from a brain region selected from the group consisting of hippocampus and cortex.

7. The method of claim 1, wherein said organotypic brain slice culture is a section of tissue from about 400 µm to about 500 µm thick.

8. The method of claim 1, wherein said organotypic brain slice culture is maintained in culture media for about 1 week to about 4 weeks prior to treatment with a test compound.

9. The method of claim 1, wherein the viability of said organotypic brain slice culture is determined by a method selected from the group consisting of: visual inspection under a microscope; staining using vital dyes stains and immunohistochemical reagents specific for cell types or moieties present in normal and injured brain; reaction with antibodies to neurofilaments, glial fibrillary acidic protein, S100, microtubule associated protein, normal or phosphorylated tau, and synaptic proteins; biochemical assessment of metabolic activity; measurement of total or specific protein content; assessment of cellular function; and assessment of neural activity.

10. The method of claim 1, wherein the viability of said organotypic brain slice culture is determined by measuring neurotransmitter secretion.

11. The method of claim 10, wherein said neurotransmitter secretion is stimulated by a method selected from the group consisting of electrical stimulation, ionic depolarization and application of neurotransmitter substance and the presence of a neurotransmitter selected from the group consisting of acetylcholine, γ-amino butyric acid (GABA), glutamate, catecholamines, and neuropeptides is determined.

12. The method of claim 1, wherein the measured amount of β-amyloid production is selected from the group consisting of any β-amyloid in the culture medium, any β-amyloid production in the organotypic brain tissue slice and deposited β-amyloid.

13. The method of claim 12, wherein the β-amyloid production in the culture medium is determined by a method selected from the group consisting of immunoprecipitation, ELISA, gel electrophoresis, and Western blotting; the β-amyloid production in the tissue slice is determined by a mnethod selected from the group consisting of immunoprecipitation, ELISA, gel electrophoresis, RIA and Western blotting; and the deposited β-amyloid production is determined by a method selected from the group consisting of biochemical determination and visual inspection and tissue section staining.

* * * * *